United States Patent [19]

Austel et al.

[11] Patent Number: 4,722,929

[45] Date of Patent: * Feb. 2, 1988

[54] NOVEL 2-PHENYL-IMIDAZOLES AND PHARMACEUTICAL COMPOSITIONS CONTAINING SAME

[75] Inventors: Volkhard Austel, Biberach; Joachim Heider, Warthausen; Norbert Hauel, Biberach; Manfred Reiffen, Biberach; Josef Nickl, Biberach; Jacobus C. A. van Meel, Biberach; Willi Diederen, Biberach, all of Fed. Rep. of Germany

[73] Assignee: Dr. Karl Thomae GmbH, Biberach an der Riss, Fed. Rep. of Germany

[*] Notice: The portion of the term of this patent subsequent to Feb. 4, 2003 has been disclaimed.

[21] Appl. No.: 684,052

[22] Filed: Dec. 20, 1984

[30] Foreign Application Priority Data

Dec. 28, 1983 [DE] Fed. Rep. of Germany ....... 3347290

[51] Int. Cl.$^4$ .................. A61K 31/435; C07D 471/04
[52] U.S. Cl. ..................................... 514/303; 546/118; 544/236; 544/267; 544/184
[58] Field of Search .................... 546/118; 514/303

[56] References Cited

U.S. PATENT DOCUMENTS

| | | | |
|---|---|---|---|
| 3,985,891 | 10/1976 | Kutter et al. | 546/118 |
| 4,327,100 | 4/1982 | Austel et al. | 546/118 |
| 4,353,909 | 10/1982 | Diederen et al. | 514/303 |
| 4,421,755 | 12/1983 | Benedikter et al. | 514/303 |
| 4,568,680 | 2/1986 | Austel et al. | 546/118 X |

FOREIGN PATENT DOCUMENTS 0079083 5/1983 European Pat. Off. .
2113675 8/1983 United Kingdom ................ 546/118

OTHER PUBLICATIONS

Middleton et al., *J. Heterocyclic Chem.*, vol. 17, pp. 1757–1760, (1980).
Haskell et al., *J. Med. Chem.*, vol. 13, No. 4, pp. 697–704, (1970).

*Primary Examiner*—Donald G. Daus
*Assistant Examiner*—William A. Teoli, Jr.
*Attorney, Agent, or Firm*—Weissenberger, Hammond & Littell

[57] ABSTRACT

The invention relates to novel 2-phenyl-imidazoles of the formula

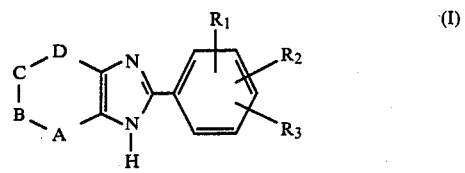

and the tautomers and acid addition salts thereof, particularly the pharmacologically acceptable acid addition salts, which exhibit valuable pharmacological properties, particularly an effect on the contractility of the heart muscle. The compounds of Formula I may be prepared by methods conventionally used for similar compounds.

11 Claims, No Drawings

NOVEL 2-PHENYL-IMIDAZOLES AND PHARMACEUTICAL COMPOSITIONS CONTAINING SAME

European patent application No. 0,079,083 describes, inter alia, the compound of the formula

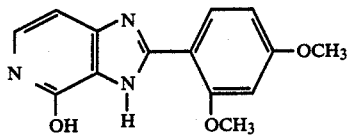

which has positive inotropic properties. It has now been found that novel 2-phenyl-imidazoles of the formula

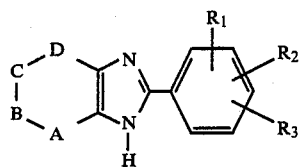

and the tautomers and acid addition salts thereof, particularly the pharmacologically acceptable acid addition salts thereof with inorganic or organic acids, which differ from the known 2-phenylimidazole derivatives either in their substituent $R_1$ or in the groups A, B, C, and D, have superior pharmacological properties, particularly an effect on the contractility of the cardiac muscle.

In Formula I above

A, B, C, and D each represent a nitrogen atom optionally substituted by a hydrogen atom or by an alkyl group having from 1 to 3 carbon atoms; a carbon atom substituted by a hydrogen atom, a halogen atom, a hydroxyl group, a benzyloxy group, or an alkoxy group having from 1 to 3 carbon atoms; or a carbonyl group, with the proviso that at least one of the groups A, B, C, and D represents a nitrogen atom optionally substituted by a hydrogen atom or an alkyl group and another of the groups A, B, C, and D represents a carbon atom substituted by a halogen atom or by a hydroxyl, benzyloxy, or alkoxy group, or a carbonyl group;

$R_1$ represents a nitrilo, aminocarbonyl, alkylaminocarbonyl, dialkylaminocarbonyl, alkoxycarbonyl, or alkanoylamino group, where each alkyl, alkoxy, or alkanoyl moiety has from 1 to 3 carbon atoms, or if A, B, C, and D together with the rest of the molecule, do not represent 8-phenyl-xanthine in which the phenyl ring is unsubstituted in the 2- and/or 6-position, $R_1$ may also represent an aminosulfonyl, alkylaminosulfonyl, or dialkylaminosulfonyl group, where each alkyl moiety may have from 1 to 3 carbon atoms, or if A represents a nitrogen atom substituted by a hydrogen atom or by an alkyl group, $R_1$ may also represent an alkylmercapto, alkylsulfinyl, or alkylsulfonyl group having from 1 to 3 carbon atoms in each alkyl moiety, or if A represents a nitrogen atom optionally substituted by a hydrogen atom or by an alkyl group and the phenyl group is substituted in the 2-position by an alkoxy or dialkylamino group, it may also represent a halogen atom or an alkyl, nitro, carboxyl, amino, alkylamino, dialkylamino, or benzyloxy group or an alkoxy group in the 5-position or else, if the groups A, B, C, and D together with the imidazole ring do not represent a theophylline group, it may also represent an alkoxy group in the 4-position, where each alkyl or alkoxy moiety may contain from 1 to 3 carbon atoms, or if A represents a nitrogen atom substituted by a hydrogen atom or by an alkyl group and $R_2$ and $R_3$ do not represent hydrogen atoms, it may also represent a halogen atom or a nitro, benzyloxy, hydroxysulfonyl, or alkoxy group, where each alkyl or alkoxy moiety has from 1 to 3 carbon atoms, or if A and at least one of the groups B and D represents a nitrogen atom optionally substituted by a hydrogen atom or by an alkyl group, $R_1$ may also represent a halogen atom or an alkyl, hydroxyl, benzyloxy, alkoxy, alkylmercapto, alkylsulfinyl, alkylsulfonyl, hydroxysulfonyl, nitro, amino, alkylamino, or dialkylamino group, where each alkyl or alkoxy moiety may have from 1 to 3 carbon atoms, or if B and C simultaneously each represent a nitrogen atom optionally substituted by a hydrogen atom or an alkyl group, $R_1$ may also represent a halogen atom or an alkyl, hydroxyl, benzyloxy, alkoxy, alkylmercapto, alkysulfinyl, alkylsulfonyl, hydroxysulfonyl, nitro, amino, alkylamino, or dialkylamino group, where each alkyl or alkoxy moiety may have from 1 to 3 carbon atoms, or if A represents a nitrogen atom and C represents a nitrogen atom substituted by an alkyl group, $R_1$ may also represent a benzyloxy, alkylmercapto, alkylsulfinyl, or alkylsulfonyl group or, if the groups A, B, C, and D together with the imidazole ring do not represent a xanthine group, $R_1$ may also represent an alkyl, hydroxyl, alkoxy, nitro, amino, alkylamino, or dialkylamino group, where each alkyl or alkoxy moiety may have from 1 to 3 carbon atoms, or if A represents a nitrogen atom and B represents a carbon atom substituted by an alkoxy group, $R_1$ may also represent a halogen atom or an alkyl, nitro, amino, alkylamino, dialkylamino, hydroxyl, alkoxy, hydroxysulfonyl, or carboxyl group, where each alkyl or alkoxy moiety may have from 1 to 3 carbon atoms; and $R_2$ and $R_3$, which may be the same or different, each represent a hydrogen atom, a halogen atom, or an alkyl, hydroxyl, alkoxy, benzyloxy, alkylmercapto, alkylsulfinyl, alkylsulfonyl, nitro, amino, alkylamino, dialkylamino, alkanoylamino, aminosulfonyl, alkylaminosulfonyl, dialkylaminosulfonyl, nitrilo, carboxyl, alkoxycarbonyl, aminocarbonyl, alkylaminocarbonyl, or dialkylaminocarbonyl group, where each alkyl, alkoxy, or alkanoyl moiety may have from 1 to 3 carbon atoms.

The present invention thus relates to the novel 2-phenylimidazo[4,5-d]pyridazin-4-ones, 2-phenyl-imidazo[4,5-b]pyridines, 2-phenyl-imidazo[4,5-b]-pyridin-5-ones, 6-hydroxy-2-phenylimidazo[4,5-c]pyridin-4-ones, 2-phenyl-imidazo[4,5-c]pyridin-4-ones, 2-phenyl-imidazo[4,5-c]pyridin-6-ones, 2-phenyl-imidazo[4,5-d]pyridazin-4,7-dione, 2-phenyl-imidazo[4,5-d]pyridazine, 2-phenyl-imidazo[4,5-c]pyridazin-6-one, 2-phenyl-imidazo[4,5-c]pyridazine, 8-phenyl-xanthine, 8-phenyl-purin-2-one, 8-phenylpurin-6-one, 8-phenyl-purine, 2-phenyl-imidazo[4,5-c]pyridine, 2-phenyl-imidazo[4,5- e]-1,2,4-triazin-6-one, 2-phenyl-imidazo[4,5-e]-1,2,4-triazine, 2-phenyl-imidazo[4,5-d]-1,2,3-triazin-7-one, 2-phenyl-imidazo[4,5-d]-1,2,3-triazine, 2-phenyl-imidazo[4,5-b]pyrazin-5-one, 2-phenyl-imidazo[4,5-b]pyrazin-5,6-dione, 2-phenyl-imidazo[4,5-b]pyrazine, 2-phenyl-imidazo[4,5-b]pyridin-7-one, 2-phenyl-imidazo[4,5-c]pyridazin-7-one, and 2-phenylimidazo[4,5-c]pyridazin-6,7-dione of Formula I above, and the tautomers and acid addition salts thereof, particularly the pharmacologically acceptable acid addition salts thereof with inorganic or organic acids. The invention also relates to pharmaceutical compositions containing these compounds and processes for preparing them.

Examples of definitions of the Groups A to D and $R_1$ to $R_3$ given hereinbefore include the following:

for the groups A to D: the nitrogen atom and the imino, methylimino, ethylimino, n-propylimino, isopropylimino, carbonyl, methine, chloromethine, bromomethine, hydroxymethine, methoxymethine, benzyloxymethine, ethoxymethine, n-propoxymethine, and isopropoxymethine groups, and for the groups $R_1$ to $R_3$: the hydrogen, fluorine, chlorine, and bromine atoms and the hydroxysulfinyl, aminosulfonyl, methylaminosulfonyl, ethylaminosulfonyl, n-propylaminosulfonyl, isopropylaminosulfonyl, dimethylaminosulfonyl, diethylaminosulfonyl, di-n-propylaminosulfonyl, methyl-ethylaminosulfonyl, ethyl-isopropylaminosulfonyl, nitrilo, aminocarbonyl, methylaminocarbonyl, ethylaminocarbonyl, n-propylaminocarbonyl, isopropylaminocarbonyl, dimethylaminocarbonyl, diethylaminocarbonyl, di-n-isopropylaminocarbonyl, methyl-ethylaminocarbonyl, ethyl-n-propylamniocarbonyl, carboxyl, methoxycarbonyl, ethoxycarbonyl, n-propoxycarbonyl, isopropoxycarbonyl, formylamino, acetylamino, propionylamino, methyl, ethyl, n-propyl, isopropyl, hydroxyl, methoxy, ethoxy, n-propoxy, benzyloxy, methylmercapto, ethylmercapto, isopropylmercapto, methylsulfinyl, ethylsulfinyl, n-propylsulfinyl, methylsulfonyl, ethylsulfonyl, isopropylsulfonyl, nitro, amino, methylamino, ethylamino, n-propylamino, dimethylamino, diethylamino, di-n-propylamino, ethyl-methylamino, and ethyl-n-propylamino groups.

Preferred compounds of Formula I above are those wherein

A, B, C, and D each represent a nitrogen atom optionally substituted by a hydrogen atom or a methyl group; a carbon atom substituted by a hydrogen, chlorine, or bromine atom or by a hydroxyl, methoxy, or benzyloxy group; or a carbonyl group, but at least one of the groups A, B, C, and D should represent a nitrogen atom substituted by a chlorine atom or by a hydroxyl, methoxy, or benzyloxy group, or a carbonyl group;

$R_1$ represents a nitrilo, aminocarbonyl, methylaminocarbonyl, dimethylaminocarbonyl, methoxycarbonyl, or acetylamino group, or if A, B, C, and D together with the rest of the molecule do not represent an 8-phenyl-xanthine in which the phenyl ring is unsubstituted in the 2- and/or 6-position, $R_1$ may also represent an aminosulfonyl, methylaminosulfonyl, or dimethylaminosulfonyl group, or if A represents a nitrogen atom substituted by a hydrogen atom or by a methyl group, $R_1$ may also represent a methylmercapto, methylsulfinyl, or methylsulfonyl group of, if A represents a nitrogen atom optionally substituted by a hydrogen atom or by a methyl group and the phenyl ring is substituted in the 2-position by a methoxy, ethoxy, propoxy, or dimethylamino group, $R_1$ may also represent a chlorine or bromine atom or a methyl, nitro, amino, methylamino, dimethylamino, or benzyloxy group or a methoxy group in the 5-position or, if the groups A, B, C, and D together with the imidazole ring do not represent a theophylline group, $R_1$ may also represent a methoxy group in the 4-position, or if A represents a nitrogen atom substituted by a hydrogen atom or a methyl group and $R_2$ and $R_3$ do not each represent a hydrogen atom, $R_1$ may also represent a chlorine or bromine atom or a nitro, hydroxysulfonyl, methoxy, ethoxy, propoxy, or benzyloxy group, or if A and at least one of the groups B and D represents a nitrogen atom optionally substituted by a hydrogen atom or a methyl group, $R_1$ may also represent a chlorine atom or a methyl, hydroxyl, benzyloxy, methoxy, ethoxy, propoxy, methylmercapto, methylsulfinyl, methylsulfonyl, hydroxysulfonyl, amino, methylamino, or dimethylamino group, or if B and C simultaneously represent a nitrogen atom optionally substituted by a hydrogen atom or by a methyl group, $R_1$ may also represent a chlorine atom or a methyl, hydroxyl, methoxy, ethoxy, propoxy, benzyloxy, methylmercapto, methylsulfinyl, methylsulfonyl, hydroxysulfonyl, nitro, amino, methylamino, or dimethylamino group, or if A represents a nitrogen atom and C represents a nitrogen atom substituted by a methyl group, $R_1$ may also represent a methylmercapto, methylsulfinyl, or methylsulfonyl group or, if the groups A, B, C, and D together with the imidazole ring do not represent an xanthine group, $R_1$ may also represent a methyl, hydroxyl, methoxy, ethoxy, propoxy, nitro, amino, methylamino, or dimethylamino group, or if A represents a nitrogen atom and B represents a carbon atom substituted by a methoxy group, $R_1$ may also represent a chlorine or bromine atom or a methyl, nitro, amino, methylamino, dimethylamino, hydroxyl, methoxy, ethoxy, propoxy, benzyloxy, methylmercapto, methylsulfinyl, methylsulfonyl, hydroxysulfonyl, or carboxyl group;

$R_2$ represents a hydrogen, chlorine, or bromine atom or a methyl, hydroxyl, methoxy, ethoxy, benzyloxy, methylmercapto, methylsulfinyl, methylsulfonyl, nitro, amino, methylamino, dimethylamino, acetylamino, aminosulfonyl, methylaminosulfonyl, methoxycarbonyl, aminocarbonyl, methylaminocarbonyl, or dimethylaminocarbonyl group; and $R_3$ represents a hydrogen atom or a dimethylamino, hydroxyl, methoxy, ethoxy, or propoxy group.

Especially preferred are those compounds wherein
$R_1$ in the 4- or 5-position is as hereinbefore defined;
$R_3$ in the 3-position is as hereinbefore defined with the proviso that $R_3$ does not represent a hydrogen atom; and
$R_2$ represents a hydrogen, chlorine, or bromine atom or a nitro, aminosulfonyl, or methylaminosulfonyl group.

Even more preferred are those compounds, wherein A, B, C, D, $R_1$, and $R_3$ are as hereinbefore defined and $R_2$ represents a hydrogen atom, particularly those compounds wherein $R_1$ in the 4-position represents a benzyloxy, methylmercapto, methylsulfinyl, methylsulfonyl, aminosulfonyl, methylaminosulfonyl, or dimethylaminosulfonyl group;
   $R_3$ in the 2-position represents a methoxy group; and
   $R_2$ represents a hydrogen atom, and the tautomers and acid addition salts thereof, particularly the pharmacologically acceptable acid addition salts thereof with inorganic or organic acids.

According to the invention, the new compounds are obtained by the following methods:

Method A

A compound of the formula

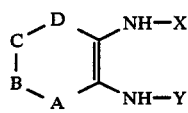

optionally prepared in the reaction mixture, wherein A to D are as hereinbefore defined and one of the groups X and Y represents a hydrogen atom and the other of the groups X and Y, or both groups X and Y, represent a group of the formula

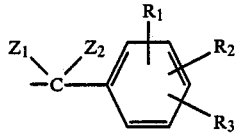

wherein $R_1$ to $R_3$ are as hereinbefore defined,
   $Z_1$ and $Z_2$, which may be identical or different, represent optionally substituted amino groups or hydroxyl or mercapto groups optionally substituted by lower alkyl groups, or
   $Z_1$ and $Z_2$ together represent an oxygen or sulfur atom, an imino group optionally substituted by an alkyl group having from 1 to 3 carbon atoms, or an alkylenedioxy or alkylenedithio group having 2 to 3 carbon atoms, is cyclized.

The cyclization is advantageously carried out in a solvent or mixture of solvents such as ethanol, isopropanol, glacial acetic acid, benzene, chlorobenzene, toluene, xylene, glycol, glycol monomethyl ether, diethylene glycol dimethyl ether, sulfolane, dimethylformamide, tetralin, or pyridine or in an excess of the acylating agent used to prepare the compound of Formula II, e.g., in the corresponding nitrile, anhydride, acid halide, ester, amide, or methoiodide, for example, at temperatures of from about 0° to 250° C., preferably at the boiling temperature of the reaction mixture, optionally in the presence of a condensing agent such as phosphorus oxychloride, thionyl chloride, sulfuryl chloride, sulfuric acid, p-toluenesulfonic acid, hydrochloric acid, phosphoric acid, polyphosphoric acid, or acetic anhydride or optionally in the presence of a base such as sodium hydroxide, postassium hydroxide, potassium ethoxide, or potassium tert.butoxide. However, cyclization may also be carried out without a solvent and/or condensing agent.

Method B

To prepare compounds of Formula I wherein at least one of the groups $R_1$, $R_2$, and $R_3$ represents an alkylsulfinyl or alkylsulfonyl group, a compound of the formula

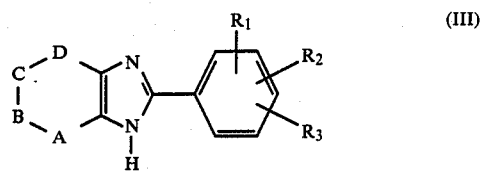

wherein A to D and $R_1$ and $R_3$ are as hereinbefore defined, with the proviso that at least one of the groups $R_1$, $R_2$, and $R_3$ must represent an alkylmercapto or alkylsulfinyl group having from 1 to 3 carbon atoms in each alkyl moiety, is oxidized.

The oxidation is preferably carried out in a solvent or mixture of solvents, e.g., in water, water/pyridine, aceton, glacial acetic acid, dilute sulfuric acid, or trifluoroacetic acid, advantageously at temperatures of from about −80° to 100° C., dependent upon the oxidizing agent used.

To prepare an alkylsulfinyl compound of Formula I, oxidation is advantageously carried out with one equivalent of the oxidizing agent used, e.g., with hydrogen peroxide in glacial acetic acid, trifluoroacetic acid, or formic acid at brom about 0° to 20° C. or in acetone at from about 0° to 60° C., with a peracid such as performic acid in glacial acetic acid or trifluoroacetic acid at from about 0° to 50° C. or with m-chloroperbenzoic acid in methylene chloride or chloroform at from about −20° C. to 60° C., with sodium metaperiodate in aqueous methanol or ethanol at from about −15° to 25° C., with bromine in glacial acetic acid or aqueous acetic acid, with N-bromo-succinimide in ethanol, with tert.butyl hypochlorite in methanol at from about −80° to −30° C., with iodobenzodichloride in aqueous pyridine at from about 0° to 50° C., with nitric acid in glacial acetic acid at from about 0° to 20° C., with chromic acid in glacial acetic acid or in acetone at from about 0° to 20°, or with sulfuryl chloride in methylene chloride at about −70° C., and the resultant thioether-chlorine complex is conveniently hydrolysed with aqueous ethanol.

To prepare an alkylsulfonyl compound of Formula I, oxidation is advantageously carried out with one or with two or more equivalents of the oxidizing agent used, e.g., with hydrogen peroxide in glacial acetic acid, trifluoroacetic acid, or formic acid at from about 20° to 100° C. or in acetone at from about 0° to 60° C., with a peracid such as performic acid or m-chloroperbenzoic acid in glacial acetic acid, trifluoroacetic acid, methylene chloride or chloroform at temperatures of from about 0° to 60° C., with nitric acid in glacial acetic acid at 0° to 20° C., or with chromic acid or potassium permanganate in glacial acetic acid, water/sulfuric acid, or acetone at from about 0° to 20° C.

Method C

To prepare compounds of Formula I wherein at least one of the groups $R_1$, $R_2$, and $R_3$ represents a hydroxysulfonyl, aminosulfonyl, alkylaminosulfonyl, or dialkylaminosulfonyl group, a compound of the formula

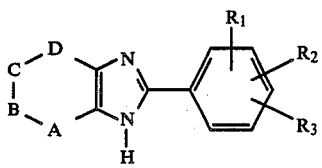 (IV)

optionally formed in the reaction mixture, wherein A to D and $R_1$ to $R_3$ are as hereinbefore defined, with the proviso that at least one of the groups $R_1$, $R_2$, and $R_3$ must represent a group of formula $USO_2$—where U represents a nucleophilic leaving group such as a halogen atom, is reacted with a compound of the formula

H—V (V)

wherein V represents a hydroxyl group or an amino group optionally substituted by one or two alkyl groups, each having from 1 to 3 carbon atoms.

The reaction is advantageously carried out in a solvent or mixture of solvents such as water, methanol, ethanol, isopropanol, methylene chloride, ether, tetrahydrofuran, dioxane, dimethylformamide, or benzene, optionally in the presence of an acid-binding agent such as sodium carbonate triethylamine, or pyridine, while these latter two may simultaneously be used as solvent as well, preferably at temperatures of from about 0° to 100° C., e.g., at temperatures of between ambient temperature and 50° C.

Method D

To prepare compounds of Formula I wherein at least one of the groups $R_1$, $R_2$, and $R_3$ represents a carbonyl group substituted by an amino, alkylamino, or dialkylamino group, a compound of the formula

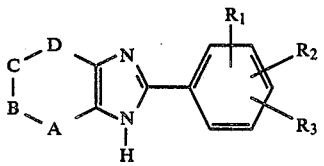 (VI)

wherein A to D and $R_1$ and $R_3$ are defined as hereinbefore, with the proviso that at least one of the groups $R_1$, $R_2$, and $R_3$ must represent the W-CO group where W represents a hydroxyl group or a nucleophilic leaving group such as a halogen atom or an aryloxy, acyloxy, or alkoxy group, or a reactive derivative thereof, is reacted with an amine of the formula

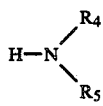 (VII)

wherein $R_4$ and $R_5$, which may be the same or different, each represent a hydrogen atom or an alkyl group having from 1 to 3 carbon atoms, or with a reactive derivative thereof if W represents the hydroxyl group.

The reaction is advantageously carried out in a solvent or mixture of solvents such as methylene chloride, chloroform, carbon tetrachloride, ether, tetrahydrofuran, dioxane, benzene, toluene, acetonitrile, or dimethylformamide, optionally in the presence of an acid-activating agent or a dehydrating agent, e.g., in the presence of ethyl chloroformate, thionyl chloride, phosphorus trichloride, phosphorus pentoxide, N,N'-dicyclohexylcarbodiimide, N,N'-carbonyldiimidazole, N,N'-thionyldiimidazole, or triphenylphosphine/carbon tetrachloride, or an agent activating the amino group, e.g., phosphorus trichloride, and optionally in the presence of an inorganic base such as sodium carbonate or a tertiary organic base such as triethylamine or pyridine, which may simultaneously act as solvent, at temperatures of from about −25° to 250° C., preferably at temperatures of between −10° C. and the boiling temperature of the solvent used. Moreover, any water formed during the reaction may be removed by azeotropic distillation, e.g., by heating with toluene using a water separator or by adding a drying agent such as magnesium sulfate or molecular sieve.

Method E

To prepare compounds of Formula I wherein at least one of the groups A, B, C, and D represents a carbon atom substituted by a hydroxyl, alkoxy, or phenylalkoxy group, or a carbonyl group, a compound of the formula

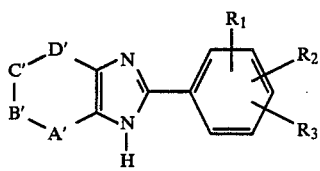 (VIII)

wherein one of the groups A', B', C', and D' represents a carbon atom substituted by a halogen atom and the others of groups A' to D' have the meanings given hereinbefore for A to D, is reacted with a compound of the formula

H—$R_6$ (IX)

wherein $R_6$ represents a hydroxyl, alkoxy, or phenylalkoxy group, where the alkyl moiety may have from 1 to 3 carbon atoms.

The reaction is advantageously carried out either in the presence of an acid such as hydrochloric, sulfuric, phosphoric, or trichloroacetic acid or in the presence of a base such as sodium hydroxide or potassium hydroxide or the alkali metal salt of a corresponding alcohol, in the melt or in a suitable solvent such as water, water/methanol, ethanol, water/ethanol, water/isopropanol, or water/dioxane at temperatures of from about −10° to 120° C., e.g., at temperatures of between ambient temperature and the boiling temperature of the reaction mixture.

During the reaction in the melt, which is advantageously carried out at temperatures of up to 200° C., any ether groups present may simultaneously be converted into hydroxyl groups.

Method F

To prepare compounds of Formula I wherein at least one of the groups A, B, C, and D represents a carbon atom substituted by a hydroxyl or carbonyl group, an N-oxide of the formula

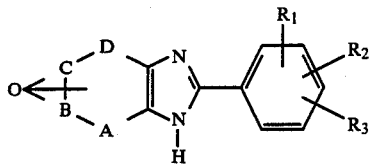

(X)

wherein A to D and R$_1$ to R$_3$ are as hereinbefore defined, is rearranged, optionally followed by hydrolysis.

The reaction is optionally carried out in a solvent such as benzene in the presence of an acylating agent such as acetic anhydride or propionic anhydride, the latter conveniently being used as solvent as well, at elevated temperatures, preferably at the boiling temperature of the solvent used.

The optional subsequent hydrolysis is conveniently carried out in water, water/methanol, water/dioxane, or methanol in the presence of an acid such as hydrochloric acid or a base such as sodium hydroxide solution or ammonia, at the boiling temperature of the reaction mixture.

Method G

To prepare compounds of Formula I wherein at least one of the groups A, B, C, and D represents a carbon atom substituted by a hydroxyl or carbonyl group and/or at least one of the groups R$_1$, R$_2$, and R$_3$ represents a hydroxyl group, a compound of the formula

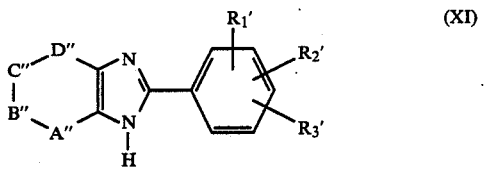

(XI)

wherein one of the groups A'', B'', C'', and D'' represents a carbon atom substituted by a benzyloxy group and the others of groups A'' to D'' have the meanings given for A to D hereinbefore, and/or at least one of the groups R$_1$', R$_2$', and R$_3$' represents a benzyloxy group and the remainder of groups R$_1$' to R$_3$' have the meanings given for R$_1$ to R$_3$ hereinbefore, is debenzylated.

The hydrogenolysis is conveniently carried out in a solvent such as methanol, ethanol, isopropanol, glacial acetic acid, ethyl acetate, dimethylformamide, or water, optionally in the presence of an inorganic acid such as hydrochloric or hydrobromic acid at temperatures of from about −10° C. to 100° C., preferably at from about 0° to 60° C., in the presence of a catalyst such as platinum, platinum oxide, or palladium on charcoal.

Method H

To prepare compounds of Formula I wherein at least one of the groups R$_1$ and R$_3$ represents an amino group, a compound of the formula

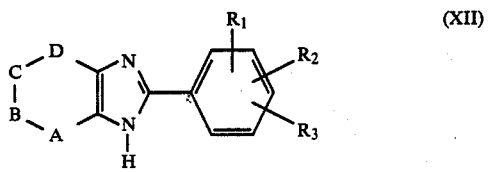

(XII)

wherein A to D are as hereinbefore defined, at least one of the groups R$_1$, R$_2$, and R$_3$ represents a group of formula

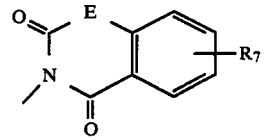

wherein E represents a bond or a methylene group optionally substituted by alkyl groups having from 1 to 3 carbon atoms and R$_7$ represents a hydrogen atom or a nitro group, and the others of groups R$_1$ to R$_3$ have the meanings given for R$_1$ to R$_3$ hereinbefore, is hydrazinolyzed.

The hydrazinolysis is advantageously carried out with hydrazine or hydrazine hydrate in a solvent such as water, methanol, ethanol, isopropanol, tetrahydrofuran, dioxane, or ethylene glycol dimethyl ether or without a solvent at temperatures of between 0° C. and the boiling temperature of the reaction mixture.

If according to the invention a compound of Formula I is obtained wherein at least one of the groups A, B, C, and D represents an alkoxymethine group and/or at least one of the groups R$_1$, R$_2$, and R$_3$ represents a cyano group, it may be converted by hydrolysis and/or alcoholysis into a corresponding compound of Formula I wherein at least one of the groups A, B, C, and D represents a carbonyl or hydroxymethine group and/or at least one of the groups R$_1$, R$_2$, and R$_3$ represents an aminocarbonyl or alkoxycarbonyl group, and/or a compound of Formula I wherein at least one of the groups R$_1$, R$_2$, and R$_3$ represents a nitro group may be converted by reduction into a corresponding compound of Formula I in which at least one of the groups R$_1$, R$_2$, and R$_3$ represents an amino group, and/or a compound of Formula I wherein at least one of the groups R$_1$, R$_2$, and R$_3$ represents an amino group may be converted by alkanolyation into a corresponding compound of Formula I in which at least one of the groups R$_1$, R$_2$, and R$_3$ represents an alkanoylamino group, and/or a compound of Formula I wherein at least one of the groups R$_1$, R$_2$, and R$_3$ represents an amino group may be converted via its diazonium salt into a corresponding compound of Formula I in which at least one of the groups R$_1$, R$_2$, and R$_3$ represents a halogen atom or a hydroxy or cyano group, and/or a compound of Formula I wherein at least one of the groups R$_1$, R$_2$, and R$_3$ represents an aminocarbonyl group may be converted by dehydration into a corresponding compound of Formula I in which R$_1$ represents a cyano group.

The subsequent hydrolysis and/or alcoholysis is carried out in the presence of an inorganic base with hydrogen peroxide, e.g., with 2N sodium hydroxide solution or potassium hydroxide solution/hydrogen peroxide, in the melt with an inorganic base, e.g., in a potassium hydroxide melt, in the presence of an acid or in the presence of an alcoholic hydrohalic acid at temperatures of from about 0° to 50° C., preferably at ambient temperature.

The subsequent reduction of the nitro compound is preferably carried out in a solvent such as water, water/ethanol, methanol, glacial acetic acid, ethyl acetate, or dimethylformamide, advantageously with hydrogen in the presence of a hydrogenation catalyst such as Raney nickel, platinum, or palladium/charcoal, with metals such as iron, tin, or zinc in the presence of an acid, with salts such as iron(II) sulfate, tin(II) chloride, or sodium dithionate, or with hydrazine in the presence of Raney nickel, at temperatures of from about 0° to 50° C., preferably at ambient temperature.

The subsequent acylation is conveniently carried out in a solvent such as methylene chloride, chloroform, carbon tetrachloride, ether, tetrahydrofuran, dioxane, benzene, toluene, acetonitrile, or dimethylformamide, preferably with a reactive derivative of the alkanoic acid, for example, with the acid chloride or the anhydride, optionally in the presence of an inorganic base such as sodium carbonate or a tertiary organic base such as triethylamine or pyridine, which may simultaneously serve as solvent, at temperatures of from about $-25°$ to 250° C., preferably at temperatures between $-10°$ C. and the boiling temperature of the solvent used.

The subsequent reaction of a diazonium salt, e.g., the fluoroborate, the fluoride in 40% hydrofluoric acid, the hydrosulfate in sulfuric acid, or the hydrochloride, if necessary in the presence of copper or a corresponding copper(I) salt such as copper(I) chloride/hydrochloric acid or copper(I) bromide/hydrobromic acid, is carried out at slightly elevated temperatures, e.g., at temperatures of from about 15° to 100° C. The diazonium salt required is appropriately prepared in a suitable solvent, e.g., in water/hydrochloric acid, methanol/hydrochloric acid, ethanol/hydrochloric acid, or dioxane/hydrochloric acid, by diazotizing a corresponding amino compound with a nitrite, e.g., sodium nitrite or an ester of nitrous acid, at low temperatures, e.g., at temperatures of from about $-10°$ to 5° C.

The subsequent dehydration is carried out with a dehydrating agent such as phosphorus pentoxide, sulfuric acid, or p-toluenesulfonic acid chloride, optionally in a solvent such as methylene chloride, or pyridine at temperatures of from about 0° to 100° C., preferably at temperatures of from about 20° to 80° C.

Moreover, the compounds of Formula I obtained may, if desired, be converted into their pharmacologically acceptable acid addition salts with inorganic or organic acids. Suitable acids include, for example, hydrochloric, hydrobromic, sulfuric, phosphoric, fumaric, succinic, tartaric, citric, lactic, maleic, and methanesulfonic acid.

The compounds of Formulae II to XII used as starting materials are known from the literature in some cases or may be obtained using methods known from the literature.

Thus, for example, the compounds of Formula II used as starting materials are obtained by acylating a corresponding o-diamino compound, and the compounds of Formulae III, IV, VI, VII, and X to XII are obtained by subsequent condensation with a corresponding benzoic acid derivative and optionally subsequent oxidation (see, European patent application No. 0,022,495).

As already mentioned hereinbefore, the novel compounds of Formula I, the 1H tautomers thereof, and the pharmacologically acceptable acid addition salts thereof have superior pharmacological properties, particularly in terms of their duration of activity, a positive inotropic activity and/or an effect on blood pressure. To demonstrate these properties, the compounds A=2-(2-Methoxy-4-methylsulfonyl-phenyl)-4H-imidazo[4,5-b]pyridin-5-one, B=2-(2-Methoxy-4-methylmercapto-phenyl)-5H-imidazo[4,5-d]pyridazin-4-one, and C=8-(2-Methoxy-4-methylmercapto-phenyl)-purin-2-one were tested for their biological properties as follows:

Determining the effect on blood pressure and the positive inotropic effect in the anaesthetised cat The tests were carried out on cats anaesthetised with sodium pentobarbital (40 mg/kg i.p.). The animals breathed spontaneously. The arterial blood pressure was measured in the aorta abdominalis with a Statham pressure transducer (P 23 Dc). To determine the positive inotropic activity, the pressure in the left ventricle was measured with a catheter-tip manometer (Millar PC-350 A). From this the contractility parameter $dp/dt_{max}$ was determined using an analogue differentiator. The test substances were injected into a vena fermoralis. The solvent used was physiological saline solution or Polydiol 200. Each substance was tested on at least 3 cats, dosage 2 mg/kg i.v.

The results are set forth in the following table:

TABLE

| Compound | Dosage (mg/kg i.v.) | Increase in $dp/dt_{max}$ (%) | Effect on Blood Pressure (mm HG) | Duration of Activity; or Half Time (in minutes) |
|---|---|---|---|---|
| A | 2.0 | +85 | −8/−7 | 14 |
| B | 2.0 | +72 | +10/+10 | 22 |
| C | 0.6 | +104 | +58/+35 | 35 |

The new compounds are well tolerated, and no toxic effects on the heart or damage to the circulation of any kind could be detected in the tests on compounds A to C.

In view of their pharmacological properties, the compounds of Formula I according to the invention and the pharmacologically acceptable acid addition salts thereof are suitable for the treatment of cardiac insufficiency of various origins since they increase the contractile force of the heart and partly by lowering blood pressure they facilitate the emptying of the heart. For this purpose the novel compounds of Formula I and the pharmacologically acceptable acid addition salts thereof, optionally in combination with other active ingredients, preferably substances which additionally guard against infection by microbes, such as sulfonamides, or antibiotics, e.g., tetracycline, doxycycline, ampicillin, amoxycillin, cephalexin, or erythromycin, may be administered to warm-blooded hosts perorally, parenterally, or rectally as active ingredients in customary preparation forms suitable for the intended purposes, that is, compositions consisting essentially of one or more inert conventional carriers and/or diluents, e.g., corn starch, lactose, glucose, microcrystalline cellulose, magnesium stearate, polyvinyl pyrrolidone, citric acid, tartaric acid, water, water/ethanol, water/glycerol, water/sorbitol, water/polyethylene, glycol, propylene glycol, carboxymethylcellulose, or fatty substances such as hard fat, or suitable mixtures thereof, and an effective amount of the active ingredient, such as tablets, coated tablets, capsules, powders, suppositories, syrups, solutions, suspensions, emulsions, ampules, and drops. Advantageously the active ingredient or a mixture of different active ingredients may be administered orally to both humans or animals, in a single dose of from about 23 to 165 mg (0.3 to 2.2 mg/kg of body weight), preferably from about 50 to 113 mg (0.7 to 1.5 mg/kg of body weight), 1 to 4 times a day. A daily dose is therefore from about 23 to 660 mg (from about 0.3 to 8.8 mg/kg of body weight), preferably from about 113 to 450 mg (from about 0.7 to 6.0 mg/kg of body weight). Dependent upon the type and severity of the affliction, upon the type of perparation, upon the route of administration, as well as upon the period or interval over which the administration takes place, it may, however, be necessary to deviate from the above dosages. Thus, it may be sufficient in some cases to administer more or less than the above-mentioned amounts of active ingredient. The optimum dosage and route of administration of active ingredient necessary in each case can easily be determined by one skilled in the art.

The following examples are intended to illustrate the invention and should not be construed as limiting the invention thereto.

EXAMPLES

EXAMPLE 1

2-(2-Methoxy-4-methylmercapto-phenyl)-5H-imidazo[4,5-d]pyridazin-4-one

Two grams of 2-methoxy-4-methylmercapto-benzoic acid are suspended in 20 ml of polyphosphoric acid, and 1.2 gm of 4,5-diamino-2H-pyridazin-3-one are added thereto with stirring at 50° C. The mixture is heated for 90 minutes to 100°–110° C. and then poured onto ice water, and the product which is precipitated on stirring is subjected to suction filtration. The mother liquor is extracted with ethyl acetate, after which the aqueous phase is made ammoniacal and extracted again with ethyl acetate. The last ethyl acetate phase is evaporated. The residue is combined with the above solid product and purified by chromatography on silica gel [eluant: methylene chloride/ethanol (100:0 to 100:3)].

Yield: 0.34 gm (12% of theory),
M.p.: 295°–300° C. (decomposition).

EXAMPLE 2

2-(2-Methoxy-4-methylsulfinyl-phenyl)-5H-imidazo[4,5-d]pyridazin-4-one

An amount of 0.21 gm of 2-(2-methoxy-4-methylmercapto-phenyl)-5H-imidazo[4,5-d]pyridazin-4-one is suspended in 10 ml of glacial acetic acid and mixed with 0.08 ml of 30% hydrogen peroxide. The mixture is stirred for 24 hours at ambient temperature and poured onto 20 ml of ice water. It is then stirred until a precipitate has formed. This is subjected to suction filtration and purified by chromatography on silica gel [eluant: methylene chloride/ethanol (100:0 to 100:3)].

Yield: 0.14 gm (63% of theory),
M.p.: 285°–288° C. (decomp.).

EXAMPLE 3

2-(2-Methoxy-4-methylsulfonyl-phenyl)-5H-imidazo[4,5-d]pyridazin-4-one

A quantity of 0.07 gm of 2-(2-methoxy-4-methylsulfinyl-phenyl)-5H-imidazo[4,5-d]pyridazin-4-one is dissolved in 5 ml of glacial acetic acid, mixed with 0.05 ml of 30% hydrogen peroxide, and stirred first for 55 minutes at ambient temperature then for two hours at 40°–50° C., Then, a further 0.05 ml of hydrogen peroxide are added, and the mixture is heated for another hour. The product precipitated is subjected to suction filtration and washed with ether.

Yield: 0.04 gm (54% of theory),
M.p.: 308°–312° C. (decomp.).

EXAMPLE 4

2-(2-Dimethylamino-4-nitro-phenyl)-5-methoxyimidazo[4,5-b]pyridine (a) 3-[(2-Dimethylamino-4-nitro-benzoyl)-amino]-2-amino-6-methoxy-pyridine An amount of 1.05 gm of 2-dimethylamino-4-nitrobenzoic acid is suspended in 35 ml of phosphorus oxychloride, and 1.05 gm of 2,3-diamino-6-methoxy-pyridine dihydrochloride are added thereto. The mixture is refluxed for 5 minutes, left to cool for 15 minutes with stirring, and finally decomposed with water. The solution obtained is cooled and poured onto a mixture of ice and concentrated ammonia. The product is then precipitated. It is subjected to suction filtration, washed with water, and dried in a circulating air drier at 50° C.

Yield: 1.5 gm (92% of theory),
M.p.: 218°–220° C. (decomp.).

(b) 2-(2-Dimethylamino-4-nitro-phenyl)-5-methoxyimidazo[4,5-b]pyridine

A suspension of 1.4 gm of 3-[(2-dimethylamino-4-nitro-benzoyl)-amino]-2-amino-6-methoxy-pyridine in 40 ml of phosphorus oxychloride is refluxed for three hours. The phosphorus oxychloride is evaporated off by about two-thirds, and the residue is poured into water. The solution obtained is made ammoniacal, and the product precipitated is purified over a silica gel column [eluant: methylene chloride/ethanol (100:0 to 100:0.5)].

Yield: 0.85 gm (64% of theory),
M.p.: 183°–186° C.

EXAMPLE 5

2-(2-Dimethylamino-4-nitro-phenyl)-5-methoxyimidazo[4,5-b]pyridine

An amount of 0.45 gm of 2-dimethylamino-4-nitrobenzoic acid is suspended in 15 ml of phosphorus oxychloride, and 0.45 gm of 2,3-diamino-6-methoxy-pyridine dihydrochloride are added. The mixture is refluxed for two hours and after cooling poured onto water. The aqueous solution is made ammoniacal with cooling, and the product precipitated is treated as in Example 4(b).

Yield: 0.3 gm (46% of theory),
M.p.: 183°–186° C.

EXAMPLE 6

2-(2-Dimethylamino-4-nitro-phenyl)-4H-imidazo[4,5-b]pyridin-5-one

A quantity of 0.2 gm of 2-(2-dimethylamino-4-nitrophenyl)-5-methoxy-imidazo[4,5-b]pyridine is heated in a bomb tube to 100° C. for three hours with 5 ml of concentrated hydrochloric acid. The reaction mixture is poured onto about 20 ml of ice, neutralized, and extracted with ethyl acetate. After washing with water and drying with magnesium sulfate, the ethyl acetate phase is evaporated. The residue is crystallized by trituration in ether/petroleum ether.

Yield: 0.06 gm (31% of theory),
M.p.: 313°–316° C. (decomp.).

EXAMPLE 7

2-(2-Methoxy-4-methylmercapto-phenyl)-4H-imidazo[4,5-b]pyridin-5-one

An amount of 6.2 gm of 2-[(2-methoxy-4-methylmercapto-benzoyl)-amino]-3-nitro-1H-pyridin-6-one is dissolved in 370 ml of glacial acetic acid and hydrogenated with hydrogen in the presence of 6 gm of 10% palladium charcoal at ambient temperature under 5 bars of pressure (duration of reaction: two hours). The catalyst is filtered off, and the filtrate is refluxed for about 1.5 hours with stirring. Then, about 250 ml of the solvent is evaporated off, and the remaining solution is poured onto ice water and neutralized with ammonia. The precipitate obtained is recrystallized from methanol. Another fraction can be obtained by evaporating the mother liquors of crystallization and triturating the residue with ether:

Yield: 3.4 gm (60% of theory),
M.p.: 274°–275° C.

EXAMPLE 8

2-(2-Methoxy-4-methylsulfinyl-phenyl)-4H-imidazo[4,5-b]pyridin-5-one

Prepared analogously to Example 2 by oxidation of 2-(2-methoxy-4-methylmercapto-phenyl)-4H-imidazo[4,5-b]pyridin-5-one.
M.p.: 250°–255° C. (decomp.).

EXAMPLE 9

2-(2-Methoxy-4-methylsulfonyl-phenyl)-4H-imidazo[4,5-b]pyridin-5-one

Prepared analogously to Example 3 by oxidation of 2-(2-methoxy-4-methylsulfinyl-phenyl)-4H-imidazo[4,5-b]pyridin-5-one.
M.p.: 300° C. (decomp.).

EXAMPLE 10

2-(2-Methoxy-4-dimethylaminosulfonyl-phenyl)-4H-imidazo[4,5-b]pyridin-5-one

Prepared analogously to Example 7 from 2-(2-methoxy-4-dimethylaminosulfonyl-benzoyl-amino)-3-nitro-1H-pyridin-6-one.
M.p.: 283°–285° C.

EXAMPLE 11

2-(2,4-Dimethoxy-5-aminosulfonyl-phenyl)-4H-imidazo[4,5-b]pyridin-5-one

A quantity of 1.36 gm of 2-(2,4-dimethoxy-phenyl)-4H-imidazo[4,5-b]pyridin-5-one is added to 5 ml of chlorosulfonic acid at 0° C., and the mixture is stirred at 20°–30° C. for 24 hours. It is poured onto ice, and the precipitate formed is filtered off. This is added in batches to 100 ml of concentrated ammonia and stirred overnight at ambient temperature. The precipitate remaining is filtered off, and the filtrate is adjusted to a pH of 5 to 6 with glacial acetic acid. The precipitate formed is centrifuged off and digested with water. The precipitate remaining is filtered off and stirred with acetone.

Yield: 0.04 gm (2% of theory),
M.p.: 280°–285° C. (decomp.).

EXAMPLE 12

2-(2,4-Dimethoxy-5-hydroxysulfonyl-phenyl)-4H-imidazo[4,5-b]pyridin-5-one

Obtained by evaporating the aqueous phase obtained on digestion according to Example 11 and recrystallizing from 2N hydrochloric acid. The product is obtained as the hemihydrate.

Yield: 0.11 gm (6% of theory),
M.p.: 295°–300° C. (decomp.).

EXAMPLE 13

2-(2,4-Dimethoxy-phenyl)-4H-imidazo[4,5-b]pyridin-5-one

Four grams of 2-(2,4-dimethoxy-phenyl)-imidazo[4,5-b]pyridin-4-oxide is suspended in 40 ml of acetic anhydride and refluxed for 2.75 hours. After cooling the mixture is poured onto 150 ml of ice, 25 ml of 6N hydrochloric acid are added, and the mixture is stirred at 120° C. for 30 minutes. It is cooled to ambient temperature, 50 ml of water are added, and the precipitate is subjected to suction filtration. The product is purified by chromatography on silica gel [eluant: methylene chloride/methanol (100:0 to 100:10)].

Yield: 3 gm (75% of theory),
M.p.: 270°–275° C. (decomp.).

EXAMPLE 14

8-(2-Methoxy-4-methylmercapto-phenyl)-1,3-dimethyl-1H,3H-purin-2,6-dione

Amounts of 8.51 gm of 4,5-diamino-1,3-dimethyl-uracil and 9.91 gm of 2-methoxy-4-methylmercapto-benzoic acid are refluxed for 5.5 hours together with 200 ml of phosphorus oxychloride. Then, any excess phosphorus oxychloride is evaporated off, and the residue is decomposed with ice water. The precipitate obtained is recrystallized from ethanol.

Yield: 14.7 gm (89% of theory),
M.p.: over 280° C.
Calculated: C, 54.20; H, 4.85; N, 16.86; S, 9.65.
Found: C, 54.24; H, 4.60; N, 16.67; S, 9.89.

EXAMPLE 15

8-(2-Methoxy-4-methylsulfinyl-phenyl)-1-3-dimethyl-1H,3H-purin-2,6-dione

A quantity of 3.7 gm of 8-(2-methoxy-4-methylmercapto-phenyl)-1,3-dimethyl-1H,3H-purin-2,6-dione is suspended in 30 ml of 50% acetic acid, and 1.8 gm of anhydrous sodium acetate are added thereto. Then, 1.6 gm of bromine (dissolved in 1.5 ml of glacial acetic acid) are added dropwise to the mixture, with stirring. The resulting mixture is stirred for a further 20 minutes, poured onto ice, and made ammoniacal, and the precipitate is recrystallized from ethanol.

Yield: 2.1 gm (55% of theory),
M.p.: 228°–229° C.

EXAMPLE 16

8-(2,4-Dimethoxy-phenyl)-1H-purin-6-one

One-half gram of 8-(2,4-dimethoxy-phenyl)-6-chloropurine is refluxed for seven hours in 30 ml of 2N sodium hydroxide solution. The mixture is acidified with glacial acetic acid, and the precipitate obtained is recrystallized from methanol.

Yield: 0.11 gm (23% of theory),
M.p.: over 270° C.
Calculated: C, 57.34; H, 4.44; N, 20.58. Found: C, 57.60; H, 4.48; N, 20.58.

EXAMPLE 17

8-(5-Aminosulfonyl-2,4-dimethoxy-phenyl)-purin-6-one

Prepared analogously to Example 16 from 6-chloro-8-(5-aminosulfonyl-2,4-dimethyl-phenyl)-purine by reaction with 20% potassium hydroxide solution.

Yield: 42% of theory,
M.p.: 262°–265° C.

EXAMPLE 18

8-(2-Methoxy-5-methylmercapto-phenyl)-purin-6-one

Prepared analogously to Example 16 from 6-chloro-8-(2-methoxy-5-methylmercapto-phenyl)-purine by reaction with 20% potassium hydroxide solution.

Yield: 53% of theory,
M.p.: 187°–190° C.

EXAMPLE 19

8-(5-Bromo-2,4-dimethoxy-phenyl)-purin-6-one

Prepared analogously to Example 16 from 6-chloro-8-(5-bromo-2,4-dimethoxy-phenyl)-purine by reaction with 20% potassium hydroxide solution.

Yield: 78.9% of theory,
M.p.: 244°–246° C.

EXAMPLE 20

8-(4-Chloro-2-methoxy-5-methylaminosulfinoyphenyl)-purin-6-one

Prepared analogously to Example 16 from 6-chloro-(4-chloro-2-methoxy-5-methylaminosulfonyl-phenyl)-purine with 20% potassium hydroxide solution.

Yield: 47% of theory,
M.p.: 213°–216° C.

EXAMPLE 21

8-(2-Methoxy-5-methylsulfinyl-phenyl)-purin-6-one

Prepared analogously to Example 2 by oxidation of 8-(2-methoxy-5-methylmercapto-phenyl)-purin-6-one.

Yield: 66% of theory,
M.p.: 203°–206° C.

EXAMPLE 22

8-(2-Methoxy-4-methylsulfinyl-phenyl)-purin-2,6-dione

Prepared analogously to Example 2 by oxidation of 8-(2-methoxy-4-methylmercapto-phenyl)-purin-2,6-dione.

Yield: 49% of theory,
M.p.: >315° C.
Calculated: C, 48.74; H, 3.77; N, 17.49; S, 10.01.
Found: C, 48.27; H, 3.72; N, 17.35; S, 9.74.

EXAMPLE 23

8-(2-Methoxy-4-methylsulfinyl-phenyl)-purin-2-one-hydrochloride

Prepared analogously to Example 2 by oxidation of 8-(2-methoxy-4-methylmercapto-phenyl)-purin-2-one hydrochloride.

Yield: 20% of theory,
M.p.: 265°–268° C. (decomp.).

EXAMPLE 24

8-(2-Methoxy-5-methylsulfonyl-phenyl)-purin-6-one

Prepared analogously to Example 3 by oxidation of 8-(2-methoxy-5-methylmercapto-phenyl)-purin-6-one with hydrogen peroxide in formic acid.

Yield: 65% of theory,
M.p.: 267°–269° C.

EXAMPLE 25

8-(2-Methoxy-4-methylsulfonyl-phenyl)-purin-2,6-dione

Prepared analogously to Example 3 by oxidation of 8-(2-methoxy-4-methylmercapto)-phenyl-purin-2,6-dione with hydrogen peroxide in formic acid.

Yield: 20% of theory,
M.p.: >315° C.
Calculated: C, 46.43; H, 3.59; N, 16.66; S, 9.53;
Found: C, 45.95; H, 3.93; N, 16.06; S, 9.84;

EXAMPLE 26

8-(2-Methoxy-4-methylmercapto-phenyl)-purin-2-one

Prepared analogously to Example 6 from 2-methoxy-8-(2-methoxy-4-methylmercapto-phenyl)-purine.

Yield: 81% of theory,
M.p.: >300° C.
Calculated: C, 54.15; H, 4.19; N, 19.43; S, 11.12.
Found: C, 53.93; H, 4.52; N, 19.39; S, 11.11.

EXAMPLE 27

8-(2-Methoxy-4-hydroxy-phenyl)-purin-2-one

Prepared analogously to Example 7 from 4-(4-benzyloxy-2-methoxy-benzoyl-amino)-5-nitro-pyrimidin-2-one.

Yield: 72% of theory,
M.p.: >330° C.
Calculated: C, 52.17; H, 4.39; N, 21.70. Found: C, 52,20; H, 4.26; N, 22.02.

EXAMPLE 28

8-(2-Methoxy-4-methylmercapto-phenyl)-purin-2,6-dione (a) 4-Amino-5-(2-methoxy-4-methylmercapto-benzoylamino)-pyrimidin-2,6-dione Twenty grams of 2-methoxy-4-methylmercapto-benzoic acid is dissolved in 260 ml of dimethylformamide, mixed with 13 gm of N,N'-carbonyl-diimidazole, and stirred for 30 minutes at ambient temperature. Then, 13 gm of 4,5-diamino-pyrimidin-2,6-dione are added, and the reaction mixture is refluxed for three hours with stirring. After cooling, it is poured into 1 liter of water. The product precipitated is suction filtered, washed with water, and dried at 70° C. in a circulating air drier.

Yield: 17.7 gm (60% of theory),
M.p.: >320° C.

(b) 8-(2-Methoxy-4-methylmercapto-phenyl)-purin-2,6-dione

Two grams of 4-amino-5-(2-methoxy-4-methylmercapto-benzoylamino)-pyrimidin-2,6-dione are refluxed for 21 hours with 50 ml of ethanol and 50 ml of 2N sodium hydroxide solution. After about 15 minutes, a solution is formed. After cooling, the solution is suction filtered with glacial acetic acid, washed with water, and dried at 70° C. in a circulating air drier. The crude product thus obtained is purified by chromatography on silica gel [eluant: methylene chloride/ethanol (19:1, 9:1, 4:1 and ethanol)].

Yield: 0.95 gm (50% of theory),
M.p.: 312°–315° C.

EXAMPLE 29

8-(2-Methoxy-4-dimethylamino-sulfonyl-phenyl)-purin-2,6-dione

Prepared analogously to Example 28(b) from 4-amino-5-(2-methoxy-4-dimethylaminosulfonyl-benzoylamino)-pyrimidin-2,6-dione.
Yield: 34% of theory,
M.p.: 323°–325° C.

EXAMPLE 30

8-(5-Aminosulfonyl-2,4-dimethoxy-phenyl)-2-methoxy-purine

Prepared analogously to Example 11 from 2-methoxy-8-(2,4-dimethoxy-phenyl)-purine.
Yield: 45% of theory,
M.p.: 267°–270° C.

EXAMPLE 31

8-(5-Aminosulfonyl-2,4-dimethoxy-phenyl)-purin-2-one

Prepared analogously to Example 6 from 2-methoxy-8-(2,4-dimethoxy-5-aminosulfonyl-phenyl)-purine.
Yield: 35% of theory (as the hydrochloride),
M.p.: 270°–272° C. (decomp.).

EXAMPLE 32

8-(2-Dimethylamino-4-nitro-phenyl)-purin-6-one

One gram of 5-amino-4-(2-dimethylamino-4-nitrobenzoylamino)pyrimidin-6-one is refluxed for two hours in 50 ml of glacial acetic acid. The mixture is evaporated to dryness, and the residue is stirred out with ethanol in the warm.
Yield: 0.52 gm (54% of theory),
M.p.: >300° C.
Calculated: C, 51.98; H, 4.03; N, 27.98. Found: C, 51.67; H, 4.10; N, 27.76.

EXAMPLE 33

8-(4-Amino-2-dimethylamino-phenyl)-purin-6-one

An amount of 0.9 gm of 8-(2-dimethylamino-4-nitrophenyl)purin-6-one is hydrogenated in 50 ml of methanol in the presence of 0.5 gm of Raney nickel at ambient temperature and under 5 bars of pressure with hydrogen for three hours until the calculated quantity has been taken up. After the catalyst has been subjected to suction filtration, the filtrate is evaporated to dryness in vacuo.
Yield: 0.74 gm (91% of theory),
M.p.: 232°–235° C.

EXAMPLE 34

8-(4-Acetamido-2-dimethylamino-phenyl)-purin-6-one

A quantity of 0.6 gm of 8-(4-amino-2-dimethylaminophenyl)purin-6-one is heated to 150° C. in 5 ml of acetic anhydride for one hour. The mixture is evaporated to dryness in vacuo and recrystallized from acetone/ether.
Yield: 0.17 gm (25% of theory),
M.p.: 278°–280° C.

EXAMPLE 35

8-(2-Methoxy-4-methylmercapto-phenyl)-purin-6-one

Prepared analogously to Example 28(b) from 4-amino-5-(2-methoxy-4-methylmercapto-benzoylamino)-pyrimidin-6-one.
Yield: 5% of theory,
M.p.: 293°–295° C.

EXAMPLE 36

8-(4-Benzyloxy-2-methoxy-phenyl)-purin-6-one

Prepared analogously to Example 16 from 8-(4-benzyloxy-2-methoxy-phenyl)-6-chloro-purine by reaction with 40% potassium hydroxide solution.
Yield: 52% of theory (as an amorphous substance),
M.p.: from 150° C.
Calculated: C, 65.51; H, 4.63; N, 16.08. Found: C, 65.28; H, 4.64; N, 16.13.

EXAMPLE 37

2-(2-Dimethylamino-4-amino-phenyl)-4H-imidazo[4,5-b]-pyridin-5-one hydrochloride An amount of 1.7 gm of 2-(2-dimethylamino-4-nitrophenyl)-4H-imidazo[4,5-b]pyridin-5-one is dissolved in 20 ml of dimethylformamide and mixed with 0.2 gm of 10% palladium/charcoal. The mixture is hydrogenated for three hours with hydrogen at ambient temperature under 5 bars of pressure. The mixture is filtered off from the catalyst, the mother liquor is mixed with 100 ml each of ether and of ethyl acetate, and finally 3 ml of etheral hydrochloric acid are added. The precipitate is recrystallized from methanol. After drying over phosphorus pentoxide and potassium hydroxide, a product is obtained which contains 1.5 mol of hydrochloric acid and 0.5 mol of water to 1 mol of base.
Yield: 0.42 gm (25% of theory),
M.p.: 225°–227° C. (decomp.).

EXAMPLE 38

2-(2-Dimethylamino-4-acetamino-phenyl)-4H-imidazo[4,5-b]pyridin-5-one

A quantity of 0.6 gm of 2-(2-dimethylamino-4-aminophenyl)imidazo[4,5-b]pyridin-5-one is refluxed with 20 ml of acetic anhydride for 30 minutes. After evaporation, 10 ml of concentrated ammnoia and then 20 ml of ice are added. The product precipitated is suction filtered and washed with water.
Yield: 0.4 gm (58% of theory),
M.p.: 309°–320° C. (decomp.).

EXAMPLE 39

8-(2-Methoxy-4-benzyloxy-phenyl)-2-benzyloxy-purine (a) 8-(2-Methoxy-4-benzyloxy-phenyl)-2-chloro-purine Prepared analogously to Example 5 from 2-chloro-4,5-diaminopyrimidine and 2-methoxy-4-benzyloxy benzoic acid.
M.p.: 245°–246° C.

(b) 8-(2-Methoxy-4-benzyloxy-phenyl)-2-benzyloxy-purine

An amount of 4.5 gm of powdered potassium hydroxide is dissolved in 70 ml of benzyl alcohol, and then 7.2 gm of 8-(2-methoxy-4-benzyloxy-phenyl)-2-chloro-purine are added. The mixture is heated to 150° C. for three hours, cooled, and filtered, the filtrate is mixed with ether, and the precipitate obtained is purified by chromatography on silica gel [eluant: methylene chloride/ethanol (100:2.5)].
Yield: 5.58 gm (65% of theory),
M.p.: 152°–153° C.

EXAMPLE 40

8-(2-Methoxy-4-hydroxy-phenyl)-3H-purin-2-one

Three grams of 8-(2-methoxy-4-benzyloxy-phenyl)-2-benzyloxypurine are dissolved in 100 ml of ethanol and hydrogenated in the presence of 1 gm of 20% palladium/charcoal for two hours at 50° C. with hydrogen at 5 bar. The catalyst is filtered off and washed with hot ethanol. The filtrates are evaporated, and the residue is triturated with methylene chloride. The solid product obtained is stirred with 30 ml of 2N sodium hydroxide solution. The solution is filtered, and the filtrate is acidified with glacial acetic acid. The precipitate formed is separated from the solution by centrifuging and purified by triturating with acetone. The product contains 1 mol of water of crystallization.

Yield: 0.22 gm (12% of theory),
M.p.: decomposition from 250° C.

EXAMPLE 41

2-(2-Methoxy-4-amino-5-nitro-phenyl)-5-methoxy-imidazo[4,5-b]pyridine

One half gram of 2-[2-methoxy-5-nitro-4-(4,4-dimethyl-7-nitro-2H,4H-isoquinolin-1,3-dione-2-yl)-phenyl]-5-methoxy-imidazo[4,5-b]pyridine is suspended in 10 ml of isopropanol, mixed with 0.5 ml of 80% hydrazine hydrate, and refluxed for 1.75 hours with stirring. The reaction mixture is concentrated by evaporation, the residue is triturated with 50 ml of ice water, and the product precipitated is purified by chromatography on silica gel [eluant: methylene chloride/ethanol (100:0 to 100:2)].

Yield: 0.18 gm (57% of theory),
M.p.: 250°–251° C. (decomp.).

EXAMPLE 42

2-(2-Methoxy-4-amino-5-nitro-phenyl)-4H-imidazo[4,5-b]pyridin-5-one hydrochloride Prepared analogously to Example 6 from 2-(2-methoxy-4-amino-5-nitro-phenyl)-5-methoxy-imidazo[4,5-b]pyridine. The product is precipitated from the reaction mixture.

M.p.: decomposition from 270° C.

EXAMPLE 43

2-(2-Methoxy-4-methylmercapto-phenyl)-7H-imidazo[4,5-e]-1,2,4-triazin-6-one

A quantity of 1.27 gm of 5,6-diamino-2H-1,2,4-triazin-3-one is refluxed for thirty minutes in 50 ml of pyridine with stirring. Then, 4.33 gm of 2-methoxy-4-methylmercapto-benzoyl chloride are added, and the mixture is refluxed for a further two hours. The percipitate is suction filtered while hot and washed with water. The solid product obtained is stirred in 2N sodium hydroxide solution for 15 minutes at ambient temperature. The solid product remaining is filtered off, the filtrate is neutralized with glacial acetic aicd, and the precipitate obtained is extracted by boiling with water.

Yield: 0.1 gm (3% of theory),
M.p.: decomposition from 317° C.

EXAMPLE 44

2-(2,4-Dimethoxy-phenyl)-7H-imidazo[4,5-e]-1,2,4-triazin-6-one

Prepared analogously to Example 43 from 5,6-diamino-2H-1,2,-4-triazin-3-one and 2,4-dimethoxybenzoyl chloride.

M.p.: decomposition from 305° C.

EXAMPLE 45

2-(2-Methoxy-4-amino-phenyl)-5H-imidazo[4,5-d]pyridazin-4-one

Prepared analogously to Example 1 from 4,5-diamino-2H-pyridazin-3-one and 2-methoxy-4-aminobenzoic acid.

M.p.: 295°–300° C. (decomp.).

EXAMPLE 46

8-(2-Methoxy-5-methylmercapto-phenyl)-3H-purin-2-one

Prepared analogously to Example 32 from 4-amino-5-(2-methoxy-5-methylmercapto-benzoylamino)-1H-pyrimidin-2-one.

M.p.: over 330° C.,
Calculated: C, 54.15; H, 4.20; N, 19.43; S, 11.12.
Found: C, 54.30; H, 4.40; N, 19.07; S, 11.28.

EXAMPLE 47

8-(2,4-Dimethoxy-5-bromo-phenyl)-3H-purin-2-one

Prepared analogously to Example 32 from 4-amino-5-(2,4-dimethoxy-5-bromo-benzoylamino)-1H-pyrimidin-2-one.

M.p.: 292°–294° C. (decomp.).

EXAMPLE 48

8-(5-Aminosulfonyl-2,4-dimethoxy-phenyl)-1H,3H-purin-2,6-dione

Prepared analogously to Example 28(b) from 4-amino-5-(5-aminosulfonyl-2,4-dimethoxy-benzoylamino)-1H,3H-pyrimidin-2,6-dione.

M.p.: 325°–328° C.

EXAMPLE 49

8-(4-Aminosulfonyl-2-methoxy-phenyl)-1H,3H-purin-2,6-dione

Prepared analogously to Example 28(b) from 4-amino-5-(4-amino-sulfonyl-2-methoxy-benzoylamino)-1H,3H-pyrimidin-2,6-dione.

M.p.: >330° C.
Calculated: C, 42.73; H, 3.29; N, 21.76; S, 9.50.
Found: C, 42.44; H, 3.50; N, 21.60; S, 9.69.

EXAMPLE 50

8-(2-Methoxy-4-methylaminosulfonyl-phenyl)-1H,3H-purin-2,6-dione

Prepared analogously to Example 28(b) from 4-amino-5-(2-methoxy-4-methylaminosulfonyl-benzoylamino)-1H,3H-pyrimidin-2,6-dione.

M.p.: 238°–240° C.

EXAMPLE 51

8-(4-Carboxy-2-methoxy-phenyl)-1H,3H-purin-2,6-dione

Prepared analogously to Example 28(b) from 4-amino-5-(4-carboxy-2-methoxybenzoylamino)-1H,3H-pyrimidin-2,6-dione.

M.p.: >330° C.

Calculated: C, 49.66; H, 3.47; N, 19.30. Found: C, 49.65; H, 3.56; N, 19.49.

EXAMPLE 52

2-(2-Propoxy-4-methylmercapto-phenyl)-5-methoxy-imidazo[4,5-b]pyridine hydrochloride Prepared analogously to Example 5 from 2,3-diamino-6-methoxypyridine dihydrochloride and 2-propoxy-4-methylmercapto-benzoic acid.

M.p.: decomposition from 178° C.

EXAMPLE 53

2-(2-Propoxy-4-methylmercapto-phenyl)-4H-imidazo[4,5-b]pyridin-5-one hydrochloride Prepared analogously to Example 6 from 2-(2-propoxy-4-methylmercapto-phenyl)-5-methoxy-imidazo[4,5-b]pyridine hydrochloride.

M.p.: 245°–247° C. (decomp.).

EXAMPLE 54

2-(2-Methoxy-4-chloro-phenyl)-5H-imidazo[4,5-d]pyridazin-4-one

An amount of 1.05 gm of 2-(2-methoxy-4-aminophenyl)-5H-imidazo[4,5-d]pyridazin-4-one is suspended in 20 ml of 6N hydrochloric acid. The suspension is cooled to 0° to −3° C., and 0.28 gm of sodium nitrite, dissolved in 2 ml of water, are added dropwise thereto. The mixture is stirred for a further 40 minutes and then heated to 80°–85° C. for one hour. The product precipitated on cooling is purified by chromatography on silica gel [eluant: first methylene chloride/ethanol (100:0 to 100:20, then 1.5 to 2.5% of glacial acetic aicd is added)].

Yield: 0.11 gm (10% of theory),

M.p.: 300°–303° C. (decomp.).

EXAMPLE 55

2-(2-Methoxy-4-hydroxy-phenyl)-5H-imidazo[4,5-d]pyridazin-4-one

The compound is obtained from the mixture described in Example 54 as the second fraction in the column separation.

Yield: 0.6 gm (57% of theory),

M.p.: 310°–315° C. (decomp.).

EXAMPLE 56

2-(2-Propoxy-4-methylsulfinyl-phenyl)-4H-imidazo[4,5-b]pyridin-5-one hydrochloride Prepared analogously to Example 2 from 2-(2-proposy-4-methylmercapto-phenyl)-4H-imidazo[4,5-b]pyridin-5-one.

M.p.: from 188° C. (decomp.).

EXAMPLE 57

2-(2-Propoxy-4-methylsulfonyl-phenyl)-4H-imidazo[4,5-b]pyridin-5-one hydrochloride Prepared analogously to Example 3 from 2-(2-propoxy-4-methylmercapto-phenyl)-4H-imidazo[4,5-b]pyridin-5-one hydrochloride.

M.p.: 312°–314° C.

EXAMPLE 58

2-(2-Methoxy-4-dimethylaminosulfonyl-phenyl)-5H-imidazo[4,5-c]-pyridin-6-one

Prepared by heating 1.1 gm of 5-amino-4-(2-methoxy-4-dimethylaminosulfonyl-benzoylamino)-1H-pyridin-2-one in 5 gm of polyphosphoric acid for two hours.

M.p.: 192°–194° C.

EXAMPLE 59

8-(2-Methoxy-4-aminosulfonyl-phenyl)-3H-purin-2-one

Prepared analogously to Example 32 from 4-amino-5-(2-methoxy-4-aminosulfonyl-benzoylamino)-3H-pyrimidin-2-one.

M.p.: 255°–257° C.

EXAMPLE 60

8-(2-Methoxy-4-methylaminosulfonyl-phenyl)-3H-purin-2-one

Prepared analogously to Example 32 from 4-amino-5-(2-methoxy-4-methylaminosulfonyl-benzoylamino)-3H-pyrimidin-2-one.

M.p.: 264°–266° C.

EXAMPLE 61

8-(2-Methoxy-4-dimethylaminosulfonyl-phenyl)-3H-purin-2-one

Prepared analogously to Example 32 from 4-amino-5-(2-methoxy-4-dimethylaminosulfonyl-benzoylamino)-3H-pyrimidin-2-one.

M.p.: 296°–298° C.

EXAMPLE 62

8-(2-Methoxy-4-cyano-phenyl)-3H-purin-2-one

Prepared analogously to Example 32 from 4-amino-5-(2-methoxy-4-cyano-benzoylamino)-3H-pyrimidin-2-one.

M.p.: 307°–309° C.

EXAMPLE 63

8-(2-Methoxy-4-aminocarbonyl-phenyl)-3H-purin-2-one

Prepared by partial saponification of 8-(2-methoxy-4-cyanophenyl)-3H-purin-2-one with concentrated sulfuric acid at ambient temperature.

M.p.: over 330° C.

Calculated: C, 54.73; H, 3.88; N, 24.55; Found: C, 54.48; H, 4.12; N, 24.36.

EXAMPLE 64

8-(2-Methoxy-4-methylsulfinyl-phenyl)-1H-purin-6-one

Prepared analogously to Example 2 from 8-(2-methoxy-4-methylmercapto-phenyl)-1H-purin-6-one.

M.p.: 273°–276° C.

EXAMPLE 65

8-(2-Methoxy-4-methylsulfonyl-phenyl)-1H-purin-6-one

Prepared analogously to Example 2 with formic acid/hydrogen peroxide from 8-(2-methoxy-4-methylmercapto-phenyl)-1H-purin-6-one.

M.p.: 309°–312° C.

EXAMPLE 66

8-(2-Methoxy-4-aminosulfonyl-phenyl)-1H-purin-6-one

Prepared analogously to Example 28(b) from 4-amino-5-(2-methoxy-4-aminosulfonyl-benzoylamino)-1H-pyrimidin-6-one.

M.p.: 294°–297° C.

EXAMPLE 67

8-(2-Methoxy-4-methylaminosulfonyl-phenyl)-1H-purin-6-one

Prepared analogously to Example 28(b) from 4-amino-5-(2-methoxy-4-methoxyaminosulfonyl-benzoylamino)-1H-pyrimidin-6-one.

M.p.: 280°–283° C.

EXAMPLE 68

8-(2-Methoxy-4-dimethylaminosulfonyl-phenyl)-1H-purin-6-one

Prepared analogously to Example 28(b) from 4-amino-5-(2-methoxy-4-dimethylaminosulfonyl-benzoylamino)-1H-pyrimidin-6-one.

M.p.: 230° C.

EXAMPLE 69

8-(2-Methoxy-4-aminocarbonyl-phenyl)-1H,3H-purin-2,6-dione

A quantity of 2.3 gm of 8-(2-methoxy-4-carboxyphenyl)-1H,-3H-purin-2,6-dione are refluxed for one hour in 50 ml of thionyl chloride with the addition of 1 drop of dimethylformamide. The excess thionyl chloride is drawn off, and the residue is stirred for 16 hours at ambient temperature with a solution of ammonia in dimethylformamide. The dimethylformamide is drawn off, the remainder is mixed with water and acidified with glacial acetic acid, and the product precipitated is filtered off.

Yield: 1.5 gm (63% of theory),
M.p.: over 320° C.
Calculated: C, 51.83; H, 3.68; N, 23.23. Found: C, 51.45; H, 3.88; N, 23.12.

EXAMPLE 70

8-(2-Methoxy-4-aminocarbonyl-phenyl)-1H-purin-6-one

Prepared analogously to Example 69 from 8-(2-methoxy-4-carboxyphenyl)-1H-purin-6-one. The compound crystallizes as the hydrate.

M.p.: Over 300° C.
Calculated: C, 48.59; H, 4.71; N, 21.80. Found: C, 48.70; H, 4.89; N, 21.60.

EXAMPLE 71

8-(2-Methoxy-4-cyano-phenyl)-1H,3H-purin-2,6-dione

Prepared by boiling 0.7 gm of 8-(2-methoxy-4-aminocarbonylphenyl)-1H,3H-purin-2,6-dione in 10 ml of phosphorus oxychloride for 24 hours. The compound crystallizes as the hemihydrate.

Yield: 0.45 gm (68% of theory),
M.p.: over 310° C.
Calculated: C, 53.48; H, 3.44; N, 23.99. Found: C, 53.60; H, 3.12; N, 23.12.

EXAMPLE 72

2-Methoxy-8-(2-methoxy-4-chloro-5-methylaminosulfonyl-phenyl)-purine

Prepared analogously to Example 11 from 2-methoxy-8-(2-methoxy-4-chloro-5-chlorosulfonyl-phenyl)-purine and aqueous methylamine solution.

M.p.: 261°–263° C.

EXAMPLE 73

8-(2-Methoxy-4-chloro-5-methylaminosulfonyl-phenyl)-3H-purin-2-one

Prepared analogously to Example 6 from 2-methoxy-8-(2-methoxy-4-chloro-5-methylaminosulfonyl-phenyl)-purine.

M.p.: 270°–272° C.

EXAMPLE 74

8-(2-Methoxy-5-methylmercapto-phenyl)-1H,3H-purin-2,6-dione

Prepared analogously to Example 28(b) from 4-amino-5-(2-methoxy-5-methylmercapto-benzoylamino)-1H,3H-pyrimidin-2,6-dione.

M.p.: 301°–303° C.

EXAMPLE 75

8-(2-Methoxy-5-methylsulfinyl-phenyl)-1H,3H-purin-2,6-dione

Prepared analogously to Example 2 from 8-(2-methoxy-5-methylmercapto-phenyl)-1H,3H-purin-2,6-dione.

M.p.: 272°–275° C.

EXAMPLE 76

8-(2-Methoxy-5-methylsulfonyl-phenyl)-1H,3H-purin-2,6-dione

Prepared analogously to Example 65 from 8-(2-methoxy-5-methylmercapto-phenyl)-1H,3H-purin-2,6-dione.

M.p.: over 320° C.
Calculated: C, 46.43; H, 3.59; N, 16.66; S, 9.53. Found: C, 45.94; H, 3.72; N, 16.53; S, 8.70.

EXAMPLE 77

2-Methoxy-8-(2-hydroxy-5-methoxy-phenyl)-purine

Prepared analogously to Example 40 from 2-methoxy-8-(2-benzyloxy-5-methoxy-phenyl)-purine. The compound crystallizes as the hydrate.

M.p.: over 300° C.
Calculated: C, 52.78; H, 4.86; N, 19.30. Found: C, 52.66; H, 4.59; N, 19.40.

EXAMPLE 78

2-Methoxy-8-(2-propyloxy-5-methoxy-phenyl)-purine

Prepared analogously to Example 28(b) from 2-methoxy-4-amino-5-(2-propyloxy-5-methoxy-benzoylamino)-pyrimidine.

M.p.: 140°–142° C.

EXAMPLE 79

8-(2-Propyloxy-5-methoxy-phenyl)-3H-purin-2-one

Prepared analogously to Example 6 from 2-methoxy-8-(2-propyloxy-5-methoxy-phenyl)-purine.
M.p.: 236°-238° C.

EXAMPLE 80

8-(2-Ethoxy-4-methoxy-phenyl)-3H-purin-2-one

Prepared analogously to Example 6 from 2-methoxy-8-(2-ethoxy-4-methoxy-phenyl)-purine.
M.p.: 250°-252° C.

EXAMPLE 81

2-Methoxy-8-(2-ethoxy-4-methoxy-phenyl)-purine

Prepared analogously to Example 28(b) from 2-methoxy-4-amino-5-(2-ethoxy-4-methoxy-benzoylamino)-pyrimidine.
M.p.: 168°-170° C.

EXAMPLE 82

8-(2-Ethoxy-4-hydroxy-phenyl)-3H-purin-2-one

Prepared analogously to Example 6 from 2-methoxy-8-(2-ethoxy-4-hydroxy-phenyl)-purine.
M.p.: 280°-283° C.

EXAMPLE 83

2-Methoxy-8-(2-ethoxy-4-hydroxy-phenyl)-purine

Prepared analogously to Example 40 from 2-methoxy-8-(2-ethoxy-4-benzyloxy-phenyl)-purine.
M.p.: 185°-188° C.

EXAMPLE 84

2-Benzyloxy-8-(2,4-dimethoxy-phenyl)-purine

Prepared analogously to Example 28(b) from 2-benzyloxy-4-amino-5-(2,4-dimethoxy-benzoylamino)-pyrimidine.
M.p.: 252°-255° C.

EXAMPLE 85

2-Methoxy-8-(2-ethoxy-5-methoxy-phenyl)-purine

Prepared analogously to Example 28(b) from 2-methoxy-4-amino-5-(2-ethoxy-5-methoxy-benzoylamino)-pyrimidine.
M.p.: 165°-168° C.

EXAMPLE 86

8-(2-Ethoxy-5-methoxy-phenyl)-3H-purin-2-one

Prepared analogously to Example 6 from 2-methoxy-8-(2-ethoxy-5-methoxy-phenyl)-purine.
M.p.: 220°-225° C.

EXAMPLE 87

8-(2-Propyloxy-4-hydroxy-phenyl)-3H-purin-2-one

Prepared analogously to Example 6 from 2-methoxy-8-(2-propyloxy-4-hydroxy-phenyl)-purine.
M.p.: 260°-263° C.

EXAMPLE 88

2-Methoxy-8-(2-methoxy-4-benzyloxy-phenyl)-purine

Prepared analogously to Example 28(b) from 2-methoxy-4-amino-5-(2-methoxy-4-benzyloxy-benzoylamino)-pyrimidine.
M.p: 156°-158° C.

EXAMPLE 89

2-Methoxy-8-(2-methoxy-4-hydroxy-phenyl)-purine

Prepared analogously to Example 40 from 2-methoxy-8-(2-methoxy-4-benzyloxy-phenyl)-purine.
M.p.: 240°-242° C.

EXAMPLE 90

1,3-Dimethyl-8-(2-methoxy-4-methylaminosulfonyl-phenyl)-1H,3H-purin-2,6-dione

Prepared analogously to Example 72 from 1,3-dimethyl-8-(2-methoxy-4-chlorosulfonyl-phenyl)-1H,3H-purin-2,6-dione.
M.p: 310°-311° C.

EXAMPLE 91

1,3-Dimethyl-8-(2-methoxy-4-dimethylaminosulfonyl-phenyl)-1H,3H-purin-2,6-dione

Prepared analogously to Example 11 from 1,3-dimethyl-8-(2-methoxy-4-chlorosulfonyl-phenyl)-1H,3H-purin-2,6-dione and dimethylamine.
M.p.: 274°-276° C.

EXAMPLE 92

2-Methoxy-8-(2-methoxy-4-chloro-phenyl)-purine

Prepared analogously to Example 28(b) from 2-methoxy-4-amino-5-(2-methoxy-4-chloro-benzoylamino)-pyrimidine.
M.p.: 280°-282° C.

EXAMPLE 93

1,3-Dimethyl-8-(2-methoxy-4-benzyloxy-phenyl)-1H,3H-purin-2,6-dione

Prepared analogously to Example 14 from 1,3-dimethyl-4,5-diamino-1H,3H-pyrimidin-2,6-dione and 2-methoxy-4-benzyloxybenzoic acid.
M.p.: 210°-213° C.

EXAMPLE 94

1,3-Dimethyl-8-(2-methoxy-4-hydroxy-phenyl)-1H,3H-purin-2,6-dione

Prepared analogously to Example 40 from 1,3-dimethyl-8-(2-methoxy-4-benzyloxy-phenyl)-1H,3H-purin-2,6-dione.
M.p.: over 310° C.
Calculated: C, 56.00; H, 4.66; N, 18.50. Found: C, 55.63; H, 4.67; N, 18.53.

EXAMPLE 95

1,3-Dimethyl-8-(2-methoxy-4-aminosulfonyl-phenyl)-1H,3H-purin-2,6-dione

Prepared analogously to Example 11 from 1,3-dimethyl-8-(2-methoxy-4-chlorosulfonyl-phenyl)-1H,3H-purin-2,6-dione.
M.p.: 304°-306° C.

EXAMPLE 96

1,3-Dimethyl-8-(2-methoxy-4-methylsulfonyl-phenyl)-1H,3H-purin-2,6-dione

Prepared analogously to Example 65 from 1,3-dimethyl-8-(2-methoxy-4-methylmercapto-phenyl)-1H,3H-purin-2,6-dione.
M.p.: 294°-297° C.

EXAMPLE 97

2-Methoxy-8-(2,4,5-trimethoxy-phenyl)-purine

Prepared analogously to Example 28(b) from 2-methoxy-4-amino-5-(2,4,5-trimethoxy-benzoylamino)-pyrimidine.

M.p.: 126°–128° C.

EXAMPLE 98

2-Methoxy-8-(2,4-dimethoxy-phenyl)-purine

Prepared analogously to Example 28(b) from 2-methoxy-4-amino-5-(2,4-dimethoxy-benzoylamino)-pyrimidine.

M.p.: 211°–213° C.

EXAMPLE 99

2-Benzyloxy-8-(2-methoxy-4methylmercapto-phenyl)-purine

Prepared analogously to Example 28(b) from 2-benzyloxy-4-amino-5-(2-methoxy-4-methylmercapto-benzoylamino)-pyrimidine.

M.p.: 278°–281° C.

EXAMPLE 100

6-Chloro-8-(2-methoxy-5-methylmercapto-phenyl)-purine

Prepared analogously to Example 14 from 4,5-diamino-6-chloropyridine and 2-methoxy-5-methylmercapto-benzoic acid.

M.p.: 172°–175° C.

EXAMPLE 101

6-Chloro-8-(2,4-dimethoxy-5-bromo-phenyl)-purine

Prepared analogously to Example 14 from 4,5-diamino-6-chloropyrimidine and 2,4-dimethoxy-5-bromo-benzoic acid.

M.p.: 260°–263° C.

EXAMPLE 102

6-Chloro-8-(2-methoxy-4-benzyloxy-phenyl)-purine

Prepared analogously to Example 28(b) from 4-amino-5-(2-methoxy-4-benzyloxy-benzoylamino)-6-chloro-pyrimidine.

M.p.: 203°–205° C.

EXAMPLE 103

2-(2-Methoxy-4-methoxycarbonyl-phenyl)-5H-imidazo[4,5-c]pyridin-4-one hydrochloride Prepared analogously to Example 1 from 2-methoxy-3,4-diaminopyridine and 2-methoxy-4-cyano-benzoic acid. The product mixture obtained is digested with dichloroethane/ethanol (3:1). The undissolved material is filtered off, and the solution is evaporated and boiled with methanolic hydrochloric acid. On cooling, the product crystallizes out in the form of the hydrate.

M.p.: 224°–226° C. (decomposition).

EXAMPLE 104

4-Methoxy-2-(2-methoxy-4-aminocarbonyl-phenyl)-imidazo[4,5-c]-pyridine

Prepared as in Example 103. The insoluble product obtained is purified over silica gel [eluant: dichloroethane/ethanol (100:0 to 95:5)].

Melting point of the hemihydrochloride: 274°276° C.

EXAMPLE 105

2-(2-Methoxy-4-aminosulfonyl-phenyl)-5H-imidazo[4,5-d]pyridazin-4-one

Prepared analogously to Example 11 from 2-(2-methoxy-4-chlorosulfonyl-phenyl)-5H-imidazo[4,5-d]pyridazin-4-one (obtained from 2-(2-methoxy-4-amino-phenyl)-5H-imidazo[4,5-d]pyridazin-4-one bu diazotizing in concentrated hydrochloric acid and treating with a solution of sulfur dioxide in glacial acetic acid in the presence of copper(II) chloride).

M.p.: 303°–304° C. (decomposition).

EXAMPLE 106

2-(2-Methoxy-4-methylaminosulfonyl-phenyl)-5H-imidazo[4,5-d]pyridazin-4-one

Prepared analogously to Example 11 from 2-(2-methoxy-4-chlorosulfonyl-phenyl)-5-H-imidazo[4,5-d]pyridazin-4-one and aqueous methylamine solution M.p.: 306°–311° C. (decomposition).

EXAMPLE 107

2-(2-Methoxy-4-dimethylaminosulfonyl-phenyl)-5H-imidazo[4,5-d]pyridazin-4-one

Prepared analogously to Example 1 from 2-methoxy-4-dimethylaminosulfonyl-benzoic acid.

M.p.: 308°–317° C. (decomposition).

EXAMPLE 108

2-(2-Methoxy-4-aminocarbonyl-phenyl)-5H-imidazo[4,5-d]pyridazin-4-one

Prepared analogously to Example 1 from 2-methoxy-4-cyanobenzoic acid.

M.p.: 317°–330° C. (decomposition).

EXAMPLE 109

2-(2-Hydroxy-4-amino-phenyl)-5H-imidazo[4,5-c]pyridazin-6-one

An amount of 0.2 gm of 2-(2-methoxy-4-aminophenyl)-6-chloroimdazo[4,5-c]pyridazine is treated with molten potassium hydroxide at 170°–190° C. for 5 minutes. The product is purified over silica gel [eluant: methylene chloride/ethanol (100:0 to 80:20)].

Yield: 170 mg (96% of theory),

M.p.: over 360° C.

EXAMPLE 110

2-(2-Methoxy-4-amino-phenyl)-6-chloro-imidazo[4,5-c]pyridazine

Prepared analogously to Example 1 from 3,4-diamino-6-chloropyridazine and 2-methoxy-4-aminobenzoic acid.

M.p.: 268°–270° C. (decomposition).

EXAMPLE 111

2-(2-Methoxy-4-acetylamino-phenyl)-5H-imidazo[4,5-d]pyridazin-4-one

Prepared analogously to Example 34 from 2-(2-methoxy-4-aminophenyl)-5H-imidazo[4,5-d]pyridazin-4-one.

M.p.: 315°–320° C. (decomposition).

EXAMPLE 112

2-(2-Methoxy-4-benzyloxy-phenyl-4-chloro-imidazo[4,5-d]pyridazine

Prepared analogously to Example 5 from 4,5-diamino-2H-pyridazin-3-one and 2-methoxy-4-benzyloxy-benzoyl chloride.

M.p.: sinters at 172°–175° C. (decomposition).

The following compounds can be prepared analogously to the preceding examples:

(i)  2-(2-Methoxy-4-cyano-phenyl)-6-chloro-5H-imidazo[4,5-c]pyridin-4-one
(ii)  2-(2-Methoxy-4-aminosulfonyl-phenyl)-5H-imidazo[4,5-c]pyridin-4-one
(iii)  2-(2-Methoxy-4-methylaminosulfonyl-phenyl)-5H-imidazo[4,5-c]pyridin-4-one
(iv) 2-(2-Methoxy-4-chloro-5-aminosulfonyl-phenyl)-5H-imidazo[4,5-c]pyridin-4-one
(v) 2-(2-Methoxy-4-methyl-5-aminosulfonyl-phenyl)-5H-imidazo[4,5-c]pyridin-4-one
(vi)  2-(2-Methoxy-4-aminosulfonyl-phenyl)-5H-imidazo[4,5-c]pyridin-6-one
(vii)  2-(2-Methoxy-4-aminosulfonyl-phenyl)-5H-imidazo[4,5-c]pyridazin-6-one
(viii)  2-(2-Methoxy-4-dimethylaminosulfonyl-phenyl)-5H-imidazo[4,5-c]pyridin-6-one
(ix)  2-(2-Methoxy-4-cyano-phenyl)-5H-imidazo[4,5-c]pyridin-4-one
(x)  2-(2-Methoxy-4-methylsulfinyl-phenyl)-7H-imidazo[4,5-e]-1,2,4-triazin-6-one
(xi)  2-(2-Methoxy-4-methysulfonyl-phenyl)-7H-imidazo[4,5-e]-1,2,4-triazin-6-one
(xii) 2-(2-Methoxy-4-cyano-phenyl)-5H-imidazo[4,5-d]pyridazin-4-one The following examples illustrate a few pharmaceutical compositions comprising a compound of the present invention as an active ingredient and represent the best modes contemplated of using the invention. The compound 8-(2-methoxy-4-methylmercaptophenyl)-purin-2-one has been used as the active substance. However, it should be understood that one or more other compounds of Formula I or tautomers or pharmacologically acceptable acid addition salts thereof can be used as active substance in place of said compound.

EXAMPLE 113

Tablets containing 100 mg of Active Substance

Each tablet has the following composition:

| Component | Amount (mg) |
| --- | --- |
| Active substance | 100.0 |
| Lactose | 50.0 |
| Polyvinyl pyrrolidone | 5.0 |
| Carboxymethylcellulose | 19.0 |
| Magnesium stearate | 1.0 |
| Total: | 175.0 |

Preparation:

The active substance and lactose are homogeneously moistened with an aqueous solution of polyvinyl pyrrolidone, passed through a screen with a mesh size of 1.5 mm, dried in a circulating air drier at 50° C., and passed through a screen with a mesh size of 1 mm. After addition of the carboxymethylcellulose and magnesium stearate, the resulting mixture is compressed to form tablets:

Weight of tablet: 175 mg

Punch: 8 mm

EXAMPLE 114

Coated Tablets containing 50 mg of Active Substance

Each tablet core has the following composition:

| Component | Amount (mg) |
| --- | --- |
| Active substance | 50.0 |
| Dried corn starch | 20.0 |
| Soluble starch | 2.0 |
| Carboxymethylcellulose | 7.0 |
| Magnesium stearate | 1.0 |
| Total: | 80.0 |

Preparation:

The active substance and starch are moistened homogeneously with an aqueous solution of the soluble starch, passed through a screen of mesh size of 1 mm, dried at 50° C. in a circulating air drier, and again passed through a 1 mm mesh screen. After addition of the carboxymethylcellulose and magnesium stearate, the mixture is pressed to form tablet cores.

Weight of core: 80 mg
Punch: 6 mm
Radius of curvature: 5 mm

The finished cores are given a sugar coating in a coating pan in the conventional manner.

Weight of coated tablet: 120 mg

EXAMPLE 115

Suppositories containing 75 mg of Active Substance

Each suppository has the following composition:

| Component | Amount (mg) |
| --- | --- |
| Active substance | 75.0 |
| Suppository mass (e.g., WITEPSOL ® H19 or W45, available from Chemische Werke Witten GmbH) | 1625.0 |
| Total: | 1700.0 |

Preparation:

The suppository mass is melted, and after the molten mass has been cooled to 38° C., ground active substance is homogeneously dispersed therein. The molten mass is then cooled to 35° C. and poured into slightly chilled suppository molds.

Weight of one suppository: 1.7 gm

EXAMPLE 116

Ampules containing 10 mg/ml of Active Substance

Each ampule contains the following:

| Component | Amount |
| --- | --- |
| Active substance | 50.0 mg |
| Ethoxylated hydroxy stearic acid | 250.0 mg |
| 1,2-Propylene glycol | 1000.0 mg |
| Distilled water q.s. ad | 5.0 ml |

Preparation:

The active substance and sorbitol are dissolved in distilled water and then made up to the given volume, and the resulting solution is filtered under sterile conditions.

Bottling: in 5 ml ampules
Sterilization: 20 minutes at 120° C.

EXAMPLE 117

Drops containing 10 mg/ml of Active Substance

One hundred milliliters of drop solution has the following composition:

| Component | Amount |
|---|---|
| Active substance | 1.0 gm |
| Methyl p-hydroxybenzoate | 0.035 gm |
| Propyl p-hydroxybenzoate | 0.015 gm |
| Anisole | 0.05 gm |
| Menthol | 0.06 gm |
| Sodium saccharin | 1.0 gm |
| Glycerol | 10.0 gm |
| Ethanol | 40.0 gm |
| Distilled water q.s. ad | 100.0 ml |

Preparation:

The benzoates are dissolved in ethanol, and then the anisole and menthol are added. The active substance, glycerol, and sodium saccharin, all dissolved in water, are then added. The solution is then filtered clear.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

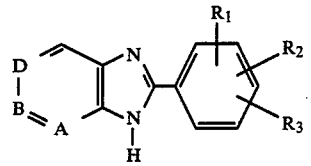

wherein
(a) A is nitrogen, B is hydroxymethine and D is methine; or
(b) B is nitrogen, one of A and D is hydroxymethine and the other is methine;

$R_1$ is methylmercapto, methylsulfinyl, methylsulfonyl, aminosulfonyl, methylaminosulfonyl or dimethylaminosulfonyl;
$R_2$ is alkoxy of 1 to 3 carbon atoms; and
$R_3$ is hydrogen or methoxy;
a pyridone tautomer thereof; or a non-toxic, pharmacologically acceptable acid addition salt thereof.

2. A compound of claim 1, which is of the formula

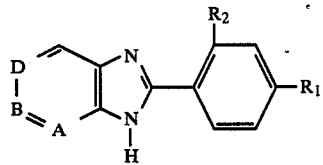

wherein
(a) A is nitrogen, B is hydroxymethine and D is methine; or
(b) B is nitrogen, one of A and D is hydroxymethine and the other is methine;

$R_1$ is methylmercapto, methylsulfinyl, methylsulfonyl, aminosulfonyl, methylaminosulfonyl or dimethylaminosulfonyl; and
$R_2$ is alkoxy of 1 to 3 carbon atoms;
a pyridone tautomer thereof; or a non-toxic, pharmacologically acceptable acid addition salt thereof.

3. A compound of claim 1, which is of the formula

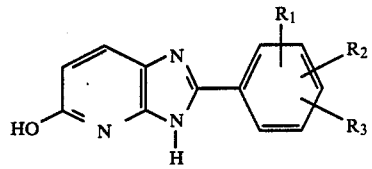

wherein
$R_1$ is methylmercapto, methylsulfinyl, methylsulfonyl, aminosulfonyl, methylaminosulfonyl or dimethylaminosulfonyl;
$R_2$ is alkoxy of 1 to 3 carbon atoms; and
$R_3$ is hydrogen or methoxy;
a pyridone tautomer thereof; or a non-toxic, pharmacologically acceptable acid addition salt thereof.

4. A compound of claim 3, which is of the formula

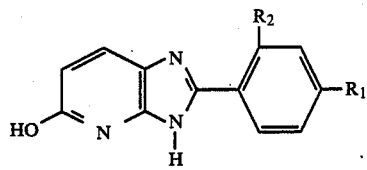

wherein
$R_1$ is methylmercapto, methylsulfinyl, methylsulfonyl, aminosulfonyl, methylaminosulfonyl or dimethylaminosulfonyl; and
$R_2$ is alkoxy of 1 to 3 carbon atoms;
a pyridone tautomer thereof; or a non-toxic, pharmacologically acceptable acid addition salt thereof.

5. A compound of claim 4, where
$R_1$ is aminosulfonyl, methylaminosulfonyl or dimethylaminosulfonyl; and
$R_2$ is methoxy;
a pyridone tautomer thereof; or a non-toxic, pharmacologically acceptable acid addition salt thereof.

6. A non-toxic, pharmacologically acceptable acid addition salt of a compound of claim 1 formed with an inorganic or organic acid.

7. A compound of claim 1, which is 2-(2-methoxy-4-methylsulfonyl-phenyl)-4H-imidazo[4,5-b]pyridine-5-one, a tautomer thereof or a non-toxic, pharmacologically acceptable acid addition salt thereof.

8. A compound of claim 1, which is 2-(2-methoxy-4-methylmercapto-phenyl)-4H-imidazo[4,5-b]pyridine-5-one, a tautomer thereof or a non-toxic, pharmacologically acceptable acid addition salt thereof.

9. A compound of claim 1, which is 2-(2-methoxy-4-dimethylaminosulfonyl-phenyl)-4H-imidazo[4,5-b]pyridine-5-one, a tautomer thereof or a non-toxic, pharmacologically acceptable acid addition salt thereof.

10. A cardiotonic pharmaceutical composition consisting essentially of an inert pharmaceutical carrier and an effective cardiotonic amount of a compound of claim 1.

11. The method of treating cardiac insufficiency in a warm-blooded animal in need of such treatment, which comprises perorally, parenterally or rectally administering to said animal an effective cardiotonic amount of a compound of claim 1.

* * * * *

UNITED STATES PATENT AND TRADEMARK OFFICE
CERTIFICATE OF CORRECTION

PATENT NO. : 4,722,929

DATED : February 2, 1988

INVENTOR(S) : Volkhard Austel et al.

It is certified that error appears in the above-identified patent and that said Letters Patent is hereby corrected as shown below:

Column 22, line 67: "pyrimdin" should read -- pyrimidin --.

Column 23, line 65: "proposy" should read -- propoxy --.

Column 29, line 68: "274°276 C" should read -- 274-276° C --.

Column 30, line 9: "bu" should read -- by --.

Column 31, line 2: Change "phenyl-4-chloro-" to
-- phenyl)-4-chloro- --.

Signed and Sealed this

Thirteenth Day of September, 1988

Attest:

DONALD J. QUIGG

*Attesting Officer*     *Commissioner of Patents and Trademarks*